United States Patent [19]

Van Geem et al.

[11] Patent Number: 4,987,265
[45] Date of Patent: Jan. 22, 1991

[54] PROCESS FOR THE PREPARATION OF BENZALDEHYDE IN THE GAS PHASE

[75] Inventors: Paul C. Van Geem, Beek; Ludovicus H. W. Janssen, Geleen, both of Netherlands

[73] Assignee: Stamicarbon B. V., Geleen, Netherlands

[21] Appl. No.: 191,053

[22] Filed: May 6, 1988

[30] Foreign Application Priority Data

May 6, 1987 [NL] Netherlands .......................... 8701063

[51] Int. Cl.$^5$ .............................................. C07C 41/00
[52] U.S. Cl. ..................................................... 568/435
[58] Field of Search ........................................... 568/435

[56] References Cited

U.S. PATENT DOCUMENTS 4,075,251 2/1978 Mertzweiller et al. ............. 568/881
4,585,899 4/1986 Gelbein et al. ...................... 568/435
4,613,700 9/1986 Maki et al. ........................... 568/435

Primary Examiner—Bruce Gray
Attorney, Agent, or Firm—Cushman, Darby & Cushman

[57] ABSTRACT

The invention relates to the preparation of a benzaldehyde by hydrogenation of a corresponding benzoic acid in the gas phase in the presence of a manganese containing catalyst on an acid carrier. The invention is characterized in that use is made of a catalyst prepared by:
(a) coprecipitation, at a pH between 7 and 10, of a manganese salt and a salt from which an acid carrier is formed,
(b) subsequent calcination at a temperature between 300° and 700° C.,
(c) followed by reduction with a hydrogen containing gas mixture.

Preferably the catalyst contains oxides of aluminum, zirconium, titanium, hafnium and/or niobium.

9 Claims, No Drawings

PROCESS FOR THE PREPARATION OF BENZALDEHYDE IN THE GAS PHASE

The invention relates to the preparation of a benzaldehyde by hydrogenation of a corresponding benzoic acid in the gas phase in the presence of a manganese-containing catalyst on an acid carrier. Such a process is known from U.S. Pat. No. 4,585,899. According to said patent specification, carboxylic acids and esters can be hydrogenated at the corresponding aldehydes with a manganese containing catlyst on active alumina. The carboxylic acids and esters may be either aliphatic or aromatic. The best results are reported for acids and esters having no hydrogen atom or atoms on the α-position. Especially benzoic acid, whether or not substituted in the aromatic nucleus, or esters thereof can be converted with a high yield. In U.S. Pat. No. 4,585,899 the manganese containing catalyst is prepared by impregnation of active alumina with an aqueous solution of a manganese salt, following which the resulting crude catalyst is dried, calcined and, optionally, reduced to its metallic form prior to use.

However, when repeating the examples of U.S. Pat. No. 4,585,899, applicant has found that the reported conversions of 75–95% are not achieved. The conversions achieved by applicant in repeating the examples remained low.

Applicant has now found that conversions of up to 100% can be achieved at selectivities that are comparable to those described in U.S. Pat. No. 4,585,899 (or that are even higher).

The process according to the invention for the preparation of a benzaldehyde by hydrogenation of a corresponding benzoic acid in the gas phase in the presence of a manganese containing catalyst on an acid carrier is characterized in that use is made of a catalyst prepared by:
(a) coprecipitation, at a pH between 7 and 10, of a manganese salt and a salt from which an acid carrier is formed,
(b) subsequent calcination at a temperature between 300° and 700° C.,
(c) followed by reduction with a hydrogen containing gas mixture.

Thus, it is achieved that benzaldehydes can be prepared in the gas phase at a very high yield, calculated as the product of conversion and selectivity.

The catalyst obtained and applied according to the invention is an oxide of manganese on an acid carrier in oxide form.

As salt from which an acid carrier is formed according to the invention, a salt can be applied from which, for instance, oxides of aluminium, zirconium, titanium, cerium, hafnium and/or niobium are formed in the catalyhst preparation. Preferably a nitrate of such an element is used.

As manganese salt it is advantageous to use manganese nitrate. When, for instance, according to the invention a catalyst is applied that is prepared by coprecipitation of manganese nitrate with aluminium nitrate, it is surprising to find that through a modified preparation method a catalyst, which as regards elementary composition is so little different from that of the state of the art as discussed above, should effect such an increase in the conversion of the benzoic acid (derivative).

The process according to the invention can be applied with a catalyst prepared with air being excluded or in the presence of air. When the catalyst is prepared with air being excluded, manganese has a lower valency than when the catalyst is prepared in the presence of air.

Using the process according to the invention, numerous benzaldehydes can be prepared, depending of course on the acid started from. Benzoic acid may, for instance, be substituted in one or more positions in the aromatic ring with an alkyl group with 1-6 C atoms, an alkoxy group with 1-6 C atoms, a hydroxy group and a halogen atom. Yet other substituents are likewise conceivable in the framework of the present invention. The substituents may be in the ortho-, the meta- as well as the para-position. As substituents, in particular the para-tertiary butyl group and the para-methoxy group are of commercial importance.

The pH of the solution from which coprecipitation takes place is 7-10, preferably 8.5-9.5.

In itself, application of a catalyst prepared by means of coprecipitation in the selective hydrogenation of a carboxylic acid to an aldehyde is known form EP-A-150,961. Here, however, it concerns a catalyst that contains zirconium dioxide as well as at least one of the elements chromium, manganese, iron, cobalt, zinc, bismuth, lead, rhenium or the elements of Group III in Periods 3-6 of the Periodic System. Optionally a carrier can be added. For the Preparation of a catalyst according to EP-A-150,961, coprecipitation is mentioned as one of the possibilities, besides impregnation, spraying and kneading. In the sole example (10) in which the catalyst is prepared by coprecipitation, an iron solution was used for coprecipitation. Information on the coprecipitation procedure is lacking. The result is not very encouraging (55% conversion). In the only example (2) in which a zirconium-manganese catalyst was applied, the catalyst was prepared by impregnation (conversion 65%).

The catalysts that can be applied according to the invention generally contain 5-50 wt. % manganese, calculated as metal. Advantageously the catalyst contains 10-35 wt. % manganese.

The process according to the invention can b e applied both batchwise and continously. The reaction temperature may vary from 300° to 700° C. and advantageously is 400°-500° C.

The pressure at which the reaction is carried out in itself is not very important, so that in general autogenous pressure can be applied.

The molar ratio of the hydrogen with respect to the benzoic acid to be hydrogenated may vary within a wide range, for instance from 1:1 to 1000:1. By preference a ratio of 50:1 to 500:1 is applied.

The benzoic acid load of the reactor, expressed as L.H.S.V., may about to 0.09-0.28 hour$^{-1}$.

The total gas load of the reactor, expressed as G.H.S.V., may amount to 4400-11500 hour$^{-1}$.

The invention will be elucidated with reference to the following examples.

Catalyst preparation A(Mn/Al

In a flask 28.3 mg Mn(NO$_3$)$_2$.4 H$_2$O and 309.5 g Al(-NO$_3$)$_3$.9 H$_2$O were dissolved in 1500 ml water. While this solution was stirred continuously, in 15 minutes a 25% solution of NH$_4$OH in water was added dropwise until the pH had become 9. During the dropwise addition the temperature was slowly from room temperature to 55° C. Subsequently, stirring was continued for another 30 minutes, and filtration and drying at 130° C.

took place. After drying, the weight of the catlayst mass was 70.2 g.

After this, the catalyst was calcined at 500° C. and reduced with hydrogen. Finally, the catalyst was crushed and screened to the desired fraction (1.2-2.0 mm cross-section). The catalyst contained 11.9 wt. % manganes,e calculated as metal.

Catalyst preparation B(Mn/Zn)

Analogous to the way described under catalyst preparation A, a manganese-on-zirconium oxide catalyst was prepared, starting from 36.2 g $Mn(NO_2.4\ H_2O$ and $ZrO(NO_3)_2.2\ H_2$ in 1500 ml water. The catalyst contained 8.5 wt. % manganese, calculated as metal.

Catalyst preparation C(Mn/Al)

Catalyst preparation A was repeated, now however air being excluded in all steps (preparation under nitrogen). The finished catalyst contained 11.9 wt. % manganese, calcualted as metal.

Catalyst preparation D(Mn/Al)

A catalyst was prepared by impregnation of gamma alumina type CK 300 of Ketjen in a solution of manganese nitrate. The amounts of the components were fhosen such that theoretically a catalyst with 12 wt. % manganese, calculated as metal, would be obtained (42.5 g gamma alumina and 28.3 g $Mn(NO_3)_2.4\ H_2O$). The mixture was heated during 2 hours at 100° C. under reflux conditions. After cooling to room temperature the excess solution was decanted and the impregnated carrier was dried at 120° C. and calcined at 450° C. Finally, the catalyst was reduced with hydrogen. The preparation method followed is, as far as could be established, in optimum conformity with the catgalyst preparation described in U.S. Pat. No. 4,585,799. Analysis of the catalyst in terms of the elements contained in it proved that the manganese content, calculated as metal, is not 11 wt. % in U.S. Pat. No. 4,585,899 19 wt. % $MnO_2$ is mentioned), but only 0.8 wt. %.

Catalyst preparation E(Mn/Al)

The catalyst was prepared as follows: 28.6 g $Mn(NO_3)_2.4\ H_2O$ was dissolved in 20 ml water. Subsequently, 43 g gamma alumina CK 300 was impregnated with this solution. A wet catalyst was formed, there being no residual free solution. Subsequently, drying took place at 120° C. By following the method described above a catalyst was obtained which, in contrast to catalyst D, did contain 11.8 wt. % manganese.

Catalyst preparation F(Mn/Al)

The preparation described under catalyst preparation A was repeated, but with 57 g $Mn(NO_3)_2.4\ H_2O$. The catalyst contained 23.9 wt. % manganese, calculated as metal.

Gas phase reaction

To a benzoic acid containing saturator, hydrogen was dosed such that the hydrogen was saturated with benzoic acid. The temperature in the saturator was 180° C. By changing the saturator temperature, for instance from 130°-200° C., the benzoic acid dose could be varied. At the outlet of the saturator, before the reactor proper, hydrogen could again be supplied.

The reactor, with a diameter of 8 mm and an internal diameter of 6 mm, contained 10 ml catalyst. Before benzoic acid was passed into the reactor, the benzoic acid/hydrogen mixture was mixed with a second hydrogen feed before being passed over the catalyst, at about reaction temperature. The amount of hydrogen applied relative to the amount of benzoic acid was 110:1 mole:mole).

After the reactor the reaction products were absorbed in a solvent (for instance DMF or ethanol) and the components were analyzed by means of chromatography.

Unless otherwise stated the experiments were performed with unsubstituted benzoic acid as the reactant.

EXAMPLE I

The reactor was charged with 10 ml catalyst obtained according to catalyst preparation A. Table 1 represents both the reaction conditions and the results.

TABLE 1

| Reaction time hour | T C | conversion benzoic acid % | selectivity to benzaldehyde % | GHSV $hr^{-1}$ | LHSV $hr^{-1}$ |
|---|---|---|---|---|---|
| 2 | 419 | 100 | 93 | 9078 | 0.17 |
| 4 | 418 | 100 | 93 | 9065 | 0.16 |
| 6 | 419 | 100 | 94 | 11446 | 0.17 |
| 8 | 419 | 100 | 94 | 11446 | 0.18 |

EXAMPLE II

The reactor was charged with 10 ml catalyst prepared according to catalyst preparation B. Table 2 presents both the reaction conditions and the results.

TABLE 2

| Reaction time hour | T C | conversion benzoic acid % | selectivity to benzaldehyde % | GHSV $hr^{-1}$ | LHSV $hr^{-1}$ |
|---|---|---|---|---|---|
| 2 | 421 | 100 | 91 | 8638 | 0.17 |
| 4 | 421 | 100 | 91 | 8638 | 0.16 |
| 6 | 422 | 100 | 91 | 8651 | 0.18 |
| 8 | 422 | 100 | 92 | 8651 | 0.19 |

COMPARATIVE EXAMPLE 1

The reactor was charged with 10 ml catalyst prepared according to catalyst preparation D. The reaction conditions and results are shown in Table 3.

TABLE 3

| Reaction time hour | T C | conversion benzoic acid % | selectivity to benzaldehyde % | GHSV $hr^{-1}$ | LHSV $hr^{-1}$ |
|---|---|---|---|---|---|
| 2 | 423 | 2 | 88 | 8406 | 0.07 |
| 4 | 423 | 3 | 95 | 8406 | 0.10 |
| 6 | 423 | 3 | 92 | 8406 | 0.09 |
| 8 | 453 | 9 | 95 | 8768 | 0.10 |
| 10 | 507 | 41 | 87 | 9420 | 0.08 |

EXAMPLE III

The reactor was charged with 10 ml catalyst prepared according to catalyst preparation C. The reaction condition are shown in Table 4.

TABLE 4

| Reaction time hour | T C | conversion benzoic acid % | selectivity to benzaldehyde % | GHSV $hr^{-1}$ | LHSV $hr^{-1}$ |
|---|---|---|---|---|---|
| 2 | 418 | 71 | 92 | 8350 | 0.18 |
| 4 | 418 | 71 | 94 | 8350 | 0.20 |
| 6 | 425 | 90 | 95 | 8430 | 0.19 |

TABLE 4-continued

| Reaction time hour | T C | conversion benzoic acid % | selectivity to benzaldehyde % | GHSV hr$^{-1}$ | LHSV hr$^{-1}$ |
|---|---|---|---|---|---|
| 8 | 433 | 100 | 91 | 8530 | 0.17 |

EXAMPLE IV

Example I was repeated starting from para-tertiary-butylbenzoic acid under reaction conditions as shown in Table 5.

TABLE 5

| Reaction time hour | T C | conversion benzoic acid % | selectivity to benzaldehyde % | GHSV hr$^{-1}$ | LHSV hr$^{-1}$ |
|---|---|---|---|---|---|
| 2 | 429 | 84 | 82 | 3835 | 0.14 |
| 4 | 429 | 90 | 92 | 8640 | 0.14 |
| 6 | 455 | 94 | 89 | 8814 | 0.15 |
| 8 | 456 | 100 | 85 | 8817 | 0.08 |

Comparative example 2

The reactor was charged with 10 ml catalyst obtained according to catalyst preparation E. Table 6 gives the reaction conditions and the results.

TABLE 6

| Reaction time hour | T C | conversion benzoic acid % | selectivity to benzaldehyde % | GHSV hr$^{-1}$ | LHSV hr$^{-1}$ |
|---|---|---|---|---|---|
| 1.5 | 423 | 37.4 | 89.2 | 8406 | 0.14 |
| 3 | 423 | 47.4 | 89.5 | 8466 | 0.16 |
| 4.5 | 450 | 73.8 | 91.0 | 8733 | 0.18 |
| 5.5 | 450 | 79.7 | 91.3 | 8732 | 0.16 |
| 7.3 | 505 | 97.1 | 76.2 | 9400 | 0.15 |
| 8.5 | 505 | 99.3 | 83.1 | 9400 | 0.12 |
| 9.8 | 505 | 98.8 | 78.3 | 9400 | 0.12 |
| 11.8 | 425 | 51.9 | 93.0 | 8406 | 0.11 |
| 12.8 | 425 | 45.2 | 93.9 | 8406 | 0.12 |

EXAMPLE V

The reactor was charged with 10 ml catalyst obtained according to catalyst preparation F. The reaction conditions and results are presented in Table 7.

TABLE 7

| Reaction time hour | T C | conversion benzoic acid % | selectivity to benzaldehyde % | GHSV hr$^{-1}$ | LHSV hr$^{-1}$ |
|---|---|---|---|---|---|
| 2 | 425 | 93.9 | 93.6 | 8990 | 0.09 |
| 3 | 425 | 95.7 | 96.7 | 8430 | 0.12 |
| 5.5 | 425 | 99.1 | 96.3 | 8430 | 0.09 |
| 9.5 | 450 | 99.5 | 84.3 | 8730 | 0.07 |
| 10.5 | 450 | 99.4 | 85.7 | 8730 | 0.08 |

We claim:

1. Process for the preparation of a substituted or unsubstituted benzaldehyde by hydrogenation of a corresponding substituted or unsubstituted benzoic acid in the gas phase in the presence of a catalyst on an acid carrier, said catalyst comprising an oxide of manganese, prepared by:
    (a) coprecipitating at a pH between 7 and 10 a manganese salt and a salt from which an acid carrier is formed;
    (b) calcining the coprecipitate obtained in step (a) at a temperature between 300° and 700° C.; and
    (c) reducing the calcined coprecipitate obtained in step (b) with a gas comprising hydrogen.

2. Process according to claim 1, wherein said substituted or unsubstituted benzoic acid is selected from the group consisting of: benzoic acid, para-tertiarybutylbenzoic acid or paramethoxybenzoic acid.

3. Process according to claim 1, wherein said acid carrier comprises one or more of: an oxide of aluminium, zirconium, titanium, cerium, hafnium and niobium.

4. Process according to claim 1, wherein said salt from which said acid carrier is formed comprises one or more salts selected from the group consisting of: a nitrate of aluminium, zirconium, titanium, cerium, hafnium and niobium.

5. Process according to claim 1, wherein said manganese nitrate comprises said manganese salt.

6. Process according to claim 1, wherein said coprecipitate is formed at a pH between 8.5 and 9.5.

7. Process according to claim 1, wherein said hydrogenation is performed in the gas phase at a temperature between 400° and 500° C.

8. Process according to claim 1, wherein said catalyst contains 5-50 wt. % manganese, calculated as metal.

9. Process according to claim 1, wherein the molar ratio of hydrogen to said substituted or unsubstituted benzoic acid to be hydrogenated is 50:1 to 500:1.

* * * * *

UNITED STATES PATENT AND TRADEMARK OFFICE
CERTIFICATE OF CORRECTION

PATENT NO. : 4,987,265

DATED : January 22, 1991

INVENTOR(S) : Paul C. VAN GEEM and Lodovicus H. W. JANSSEN

Page 1 of 2

It is certified that error appears in the above-identified patent and that said Letters Patent is hereby corrected as shown below:

Column 2, line 26, change "Preparation" to --preparation--;

line 42, change "b e" to --be--;

line 54, after "may" insert --amount--; and line 66, after "slowly" insert --raised--.

Column 3, line 13, change "$H_2$" to --$H_2O$--;

line 26, change "fhosen" to --chosen--;

line 35, change "catgalyst" to --catalyst--; and line 48, after "120°C" insert --and calcination at 500°C--.

Column 4, line 21, in Table 1, change "C" to --°C--;

line 35, in Table 2, change "C" to --°C--;

line 50, in Table 3, change "C" to --°C--;

UNITED STATES PATENT AND TRADEMARK OFFICE
CERTIFICATE OF CORRECTION

PATENT NO. : 4,987,265

DATED : January 22, 1991

INVENTOR(S) : Paul C. VAN GEEM and Lodovicus H. W. JANSSEN

It is certified that error appears in the above-identified patent and that said Letters Patent is hereby corrected as shown below:

Column 2, line 65, in Table 4, change "C" to --°C--.

Column 5, line 5, in Table 4, change "C" to --°C--;

line 18, in Table 5, change "C" to --°C--; and line 33, in Table 6, change "C" to --°C--.

Signed and Sealed this

Fifth Day of January, 1993

Attest:

DOUGLAS B. COMER

Attesting Officer     Acting Commissioner of Patents and Trademarks